US00PP26199P2

(12) United States Plant Patent
Noordhuis et al.

(10) Patent No.: US PP26,199 P2
(45) Date of Patent: Dec. 8, 2015

(54) ***CAREX* PLANT NAMED 'ET CRX01'**

(50) Latin Name: *Carex hybrida*
Varietal Denomination: ET CRX01

(71) Applicants: Bart Noordhuis, Boijl (NL); Elisabeth Bisschop, Boijl (NL)

(72) Inventors: Bart Noordhuis, Boijl (NL); Elisabeth Bisschop, Boijl (NL)

(73) Assignee: Eternal Plant Boijl B.V., Boijl (NL)

( * ) Notice: Subject to any disclaimer, the term of this patent is extended or adjusted under 35 U.S.C. 154(b) by 67 days.

(21) Appl. No.: 13/999,423

(22) Filed: Feb. 25, 2014

(51) Int. Cl.
*A01H 5/00* (2006.01)

(52) U.S. Cl.
USPC ..... Plt./384

(58) Field of Classification Search
USPC ..... Plt./384
See application file for complete search history.

*Primary Examiner* — Annette Para
(74) *Attorney, Agent, or Firm* — C. A. Whealy

(57) ABSTRACT

A new and distinct cultivar of *Carex* plant named 'ET CRX01', characterized by its relatively compact and broad outwardly arching plant habit; moderately vigorous to vigorous growth habit; long lanceolate variegated leaves with green-colored centers and white-colored margins; and good postproduction longevity and garden performance.

1 Drawing Sheet

Botanical designation: *Carex hybrida.*
Cultivar denomination: 'ET CRX01'.

BACKGROUND OF THE INVENTION

The present invention relates to a new and distinct *Carex* plant, botanically known as *Carex hybrida* and hereinafter referred to by the name 'ET CRX01'.

The new Helleborus plant is a product of a planned breeding program conducted by the Inventors in Boijl, The Netherlands. The objective of the breeding program was to create new *Carex* plants with an elegant plant habit and variegated leaves.

The new *Carex* plant originated from a cross-pollination conducted by the Inventors in Boijl, The Netherlands in 2010 of a proprietary selection of *Carex hybrida* identified as code number 520, as the female, or seed, parent, not patented, with a proprietary selection of *Carex hybrida* identified as code number 6-90, as the male, or pollen, parent, not patented. The new *Carex* plant was discovered and selected by the Inventors as a single plant from within the progeny of the stated cross-pollination grown in a controlled greenhouse environment in Boijl, The Netherlands in January, 2011.

Asexual reproduction of the new *Carex* plant by divisions in a controlled greenhouse environment in Boijl, The Netherlands since January, 2011 has shown that the unique features of this new *Carex* plant are stable and reproduced true to type in successive generations.

SUMMARY OF THE INVENTION

Plants of the new *Carex* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'ET CRX01'.

These characteristics in combination distinguish 'ET CRX 01' as a new and distinct *Carex* plant:

1. Relatively compact and broad outwardly arching plant habit.
2. Moderately vigorous to vigorous growth habit.
3. Long lanceolate variegated leaves with green-colored centers and white-colored margins.
4. Good postproduction longevity and garden performance.

Plants of the new *Carex* differ primarily from plants of the female parent selection in the following characteristics:

1. Leaves of plants of the new *Carex* are longer than leaves of plants of the female parent selection.
2. Leaves of plants of the new *Carex* are variegated whereas leaves of plants of the female parent selection are solid green in color.

Plants of the new *Carex* differ primarily from plants of the male parent selection in the following characteristics:

1. Leaves of plants of the new *Carex* are shorter than leaves of plants of the male parent selection.
2. Leaves of plants of the new *Carex* are variegated whereas leaves of plants of the male parent selection are solid green in color.

Plants of the new *Carex* can be compared to plants of the *Carex oshimensis* 'Everoro', disclosed in U.S. Plant Pat. No. 23,406. In side-by-side comparisons conducted in Boijl, The Netherlands, plants of the new *Carex* differed primarily from plants of 'Everoro' in the following characteristics:

1. Plants of the new *Carex* were more compact than plants of 'Everoro'.
2. Plants of the new *Carex* and 'Everoro' differed in color as plants of 'Everoro' had green and yellow variegated leaves.

BRIEF DESCRIPTION OF THE PHOTOGRAPH

The accompanying photograph illustrates the overall appearance of the new *Carex* plant showing the colors as true as it is reasonably possible to obtain in colored reproductions of this type. Colors in the photograph may differ slightly from the color values cited in the detailed botanical description which accurately describe the colors of the new *Carex* plant.

The photograph comprises side perspective view of a typical plant of 'ET CRX01' grown in a container.

DETAILED BOTANICAL DESCRIPTION

The aforementioned photograph and following observations and measurements describe plants grown during the spring in 26-cm containers in an outdoor nursery in Boijl, The Netherlands and under cultural practices typical of commercial *Carex* plant production. During the production of the plants, day temperatures ranged from 18° C. to 32° C. and night temperatures ranged from 6° C. to 20° C. Plants were three years old when the photograph and botanical description were taken. In the following description, color references are made to The Royal Horticultural Society Colour Chart, 2001 Edition, except where general terms of ordinary dictionary significance are used.

Botanical classification: *Carex hybrida* 'ET CRX01'.

Parentage:

*Female, or seed, parent*.—Proprietary selection of *Carex hybrida* identified as code number 520, not patented.

*Male, or pollen, parent*.—Proprietary selection of *Carex hybrida* identified as code number 6-90, not patented.

Propagation:

*Type*.—By divisions.

*Time to initiate roots, summer and winter*.—About six weeks at temperatures about 20° C.

*Time to produce a rooted young plant, summer and winter*.—About three months at temperatures about 20° C.

*Root description*.—Medium in thickness, fleshy; color, close to 162D.

*Rooting habit*.—Freely branching habit; medium density.

Plant description:

*Plant and growth habit*.—Relatively compact and broad outwardly arching plant habit; about 30 main shoots develop from the base; moderately vigorous to vigorous growth habit; moderate to fast growth rate.

*Plant height, soil level to top of foliar plane*.—About 32 cm.

*Plant length, lowermost leaf apex to top of foliar plane*.—About 75 cm.

*Plant diameter or spread*.—About 81.5 cm.

Leaf description:

*Arrangement*.—Alternate; sessile.

*Length*.—About 74.5 cm.

*Width*.—About 1.2 cm.

*Shape*.—Lanceolate; strongly curved and arching.

*Apex*.—Long acuminate to long aristate.

*Margin*.—Very finely serrate.

*Base*.—Sheathing.

*Texture, upper and lower surfaces*.—Smooth, glabrous.

*Luster, upper surface*.—Glossy.

*Luster, lower surface*.—Moderately glossy.

*Venation pattern*.—Parallel.

*Color*.—Developing leaves, upper surface: Center, between 143B and 144A; margins and narrow longitudinal stripes, close to 151D and 154C. Developing leaves, lower surface: Center, close to 143A to 143B; margins and narrow longitudinal stripes, close to 154C to 154D. Fully expanded leaves, upper surface: Center, close to 137A to 137B; margins and narrow longitudinal stripes, between 155C and 157D. Fully expanded leaves, lower surface: Center, between 138A and 146A; margins and narrow longitudinal stripes, between 150D and 157D. Venation, upper surface: Close to 137A to 137B. Venation, lower surface: Between 138A and 146A.

Flower description: Flower initiation and development has not been observed on plants of the new *Carex*.

Disease & pest resistance: Plants of the new *Carex* have not been shown to be resistant to pathogens and pests common to *Carex* plants.

Postproduction longevity: Good postproduction longevity, plants of the new *Carex* are durable and maintain good leaf substance for about three months.

Garden performance: Plants of the new *Carex* have been observed to have good garden performance and to tolerate wind, rain and temperatures ranging from about −20° C. to about 35° C.

It is claimed:

1. A new and distinct *Carex* plant named 'ET CRX01' as illustrated and described.

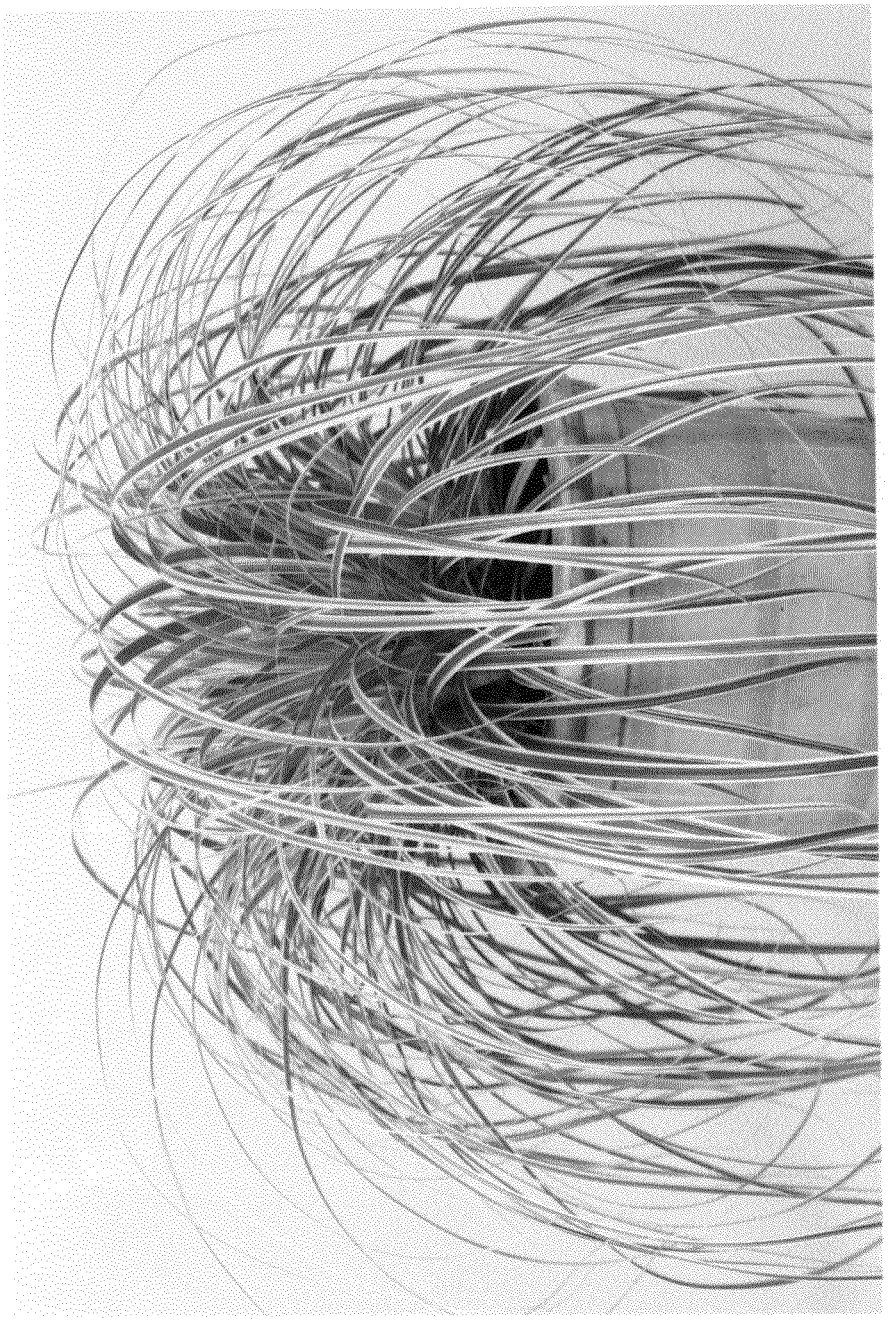

* * * * *